(12) United States Patent
Willmann

(10) Patent No.: US 7,699,881 B2
(45) Date of Patent: Apr. 20, 2010

(54) BONE SCREW

(75) Inventor: Niko Willmann, Ulm (DE)

(73) Assignee: Ulrich GmbH & Co. LG, Ulm (DE)

( * ) Notice: Subject to any disclaimer, the term of this patent is extended or adjusted under 35 U.S.C. 154(b) by 0 days.

(21) Appl. No.: 10/575,673

(22) PCT Filed: Oct. 29, 2004

(86) PCT No.: PCT/DE2004/002417

§ 371 (c)(1),
(2), (4) Date: Apr. 11, 2006

(87) PCT Pub. No.: WO2005/041798

PCT Pub. Date: May 12, 2005

(65) Prior Publication Data

US 2007/0043372 A1    Feb. 22, 2007

(30) Foreign Application Priority Data

Oct. 29, 2003    (DE) ............................. 103 50 424

(51) Int. Cl.
*A61B 17/86* (2006.01)
(52) U.S. Cl. ..................................... 606/309
(58) Field of Classification Search .............. 606/72, 606/73, 300–321; 411/411, 417, 418, 421
See application file for complete search history.

(56) References Cited

U.S. PATENT DOCUMENTS

| 1,235,626 | A |   | 8/1917  | Woodward |        |
|-----------|---|---|---------|----------|--------|
| 4,468,200 | A | * | 8/1984  | Munch .................... | 433/174 |
| 5,269,685 | A | * | 12/1993 | Jorneus et al. .............. | 433/174 |
| 5,334,204 | A |   | 8/1994  | Clewett et al. |         |
| 5,727,943 | A | * | 3/1998  | Beaty et al. ................. | 433/174 |
| 6,196,842 | B1 | * | 3/2001 | Jorneus ...................... | 433/174 |
| 6,679,701 | B1 |   | 1/2004 | Blacklock |         |
| 6,758,672 | B2 | * | 7/2004 | Porter et al. ................. | 433/173 |
| 6,896,517 | B1 | * | 5/2005 | Bjorn et al. ................. | 433/174 |
| 2002/0055783 | A1 |   | 5/2002 | Tallarida et al. |     |
| 2004/0006346 | A1 | * | 1/2004 | Holmen et al. ................ | 606/73 |
| 2004/0210227 | A1 | * | 10/2004 | Trail et al. .................... | 606/73 |

FOREIGN PATENT DOCUMENTS

WO    WO 93/06786    4/1993

\* cited by examiner

*Primary Examiner*—Thomas C Barrett
*Assistant Examiner*—Michael J Araj
(74) *Attorney, Agent, or Firm*—Andrew Wilford

(57) ABSTRACT

The invention concerns a bone screw comprising a head (2), a stem (3) and a thread (4) provided in the form of turns on the stem (3). A plurality of first turns (6) comprising smooth cutting edges (7) extend towards the head (2) from the free end (5) of the stem (3). Second turns (8) adjacent to the first turns (6), arranged in steps towards the head (2), comprise recesses (9) provided in the cutting edges (7). The size of the recesses (9) of the second turns (8) gradually increases from the free end (5) while the are of the edges in the peripheral direction gradually decreases.

9 Claims, 5 Drawing Sheets

BONE SCREW

CROSS REFERENCE TO RELATED APPLICATIONS

This application is the US national phase of PCT application PCT/DE2004/002417, filed 29 Oct. 2004, published 12 May 2005 as WO 2005/041798, and claiming the priority of German patent application 10350424.9 itself filed 29 Oct. 2003, whose entire disclosures are herewith incorporated by reference.

FIELD OF THE INVENTION

The invention relates to a bone screw, especially spongiosis screw, having a screw head, a screw shank and a screwthread formed on the screw shank by a plurality of turns.

BACKGROUND OF THE INVENTION

Bone screws are known from practice that are used in medicine to rejoin bones after a fracture, to anchor bone plates, or, in the case of spongiosis screws, to anchor implants to vertebrae. Such bone screws often remain permanently in the body of the patient and thus have to perform their intended function for a long period of time without detaching under load.

OBJECT OF THE INVENTION

Thus, the object of the invention is to design a bone screw of the above-mentioned type such that, after being screwed in, undesired position changes, especially detachment, are prevented.

SUMMARY OF THE INVENTION

This object is solved according to invention with a bone screw of the above-mentioned type in that starting from the free end of the screw shank there is a first screwthread with smooth cutting edges extend toward the screw head, that a second screwthread extends from the first screwthread are formed toward of the screw head with recesses formed in the cutting edges, and that the recesses of the second screwthread relative to the angular length in circumferential direction are increased compared to the second screwthread away from the free end.

Such a bone screw ensures that with when screwed into the bone a good anchoring of the bone screw in the bone is achieved through the first screwthread already on a short guiding length while making a clean cut with the smooth cutting edges of the first screwthread that the following cutting edges of the second screwthread can pass through. The recesses of the second screwthread effect thereby according to their barbed shape a stronger engagement of the screw shank into the bone and ensure that, after the screwing into the bone, body tissue, i.e. bone material, can grow into the cutting path in the area of the recesses and thus block detachment of the bone screw by unscrewing of the thread back along the cutting channel.

In the scope of the invention it is preferred, that a third screwthread extending from the second screwthread is formed with recesses of constant size. This has the advantage that the length of the bone screw can be varied in a simple way by a variation of the number of turns of the third screwthread, without having to shorten the cutting edges in the area of the screw head by progression of the length through the increasing broadening of the recesses of the second screwthread, such that their function is endangered.

It has been proven advantageous when in the second screwthread and in the third screwthread on an arc of 360° several recesses, preferably three recesses, are formed, to obtain a firm fit of the bone screw, and to enable, with a constant spacing of the recesses around the perimeter of the screw shank, a constant rotational movement of the bone screw with its screwing.

An especially firm fit of the bone screw in the bone is achieved, when the recess extends chordally toward the screw shank from the cutting edge of the second screwthread and of the third screwthread and joins in an arc again the cutting edge.

In the scope of the invention there is the possibility, that the screw shank has a cylindrical form, wherein the advantage of the first screwthread is especially clearly distinct, which establish the screw channel, through which from the surface of the bone also the second screwthread and the third screwthread can be screwed. There is also the possibility, that the screw shank has a tapered form, to achieve that also the second screwthread and third screwthread work themselves into the bone material and thus give a firm fit. To execute the intended function of the first screwthread it is sufficient, when the first screwthread comprises three turns. It is also sufficient, when the second screwthread comprises three turns.

In the case of screws with a screw shank in a tapered form it is possible that the lengths of the cutting edges of the turns of the second screwthread are constant, i.e. that the broadening of the circumferential length of the turns lying closer to the screw head is assigned to the recesses to have a good guiding through sufficiently long cutting edges despite of the given advantage through increasing recesses.

BRIEF DESCRIPTION OF THE DRAWING

In the following the invention is explained in more detail at an embodiment represented in the drawing; therein.

SPECIFIC DESCRIPTION

Figure 1:
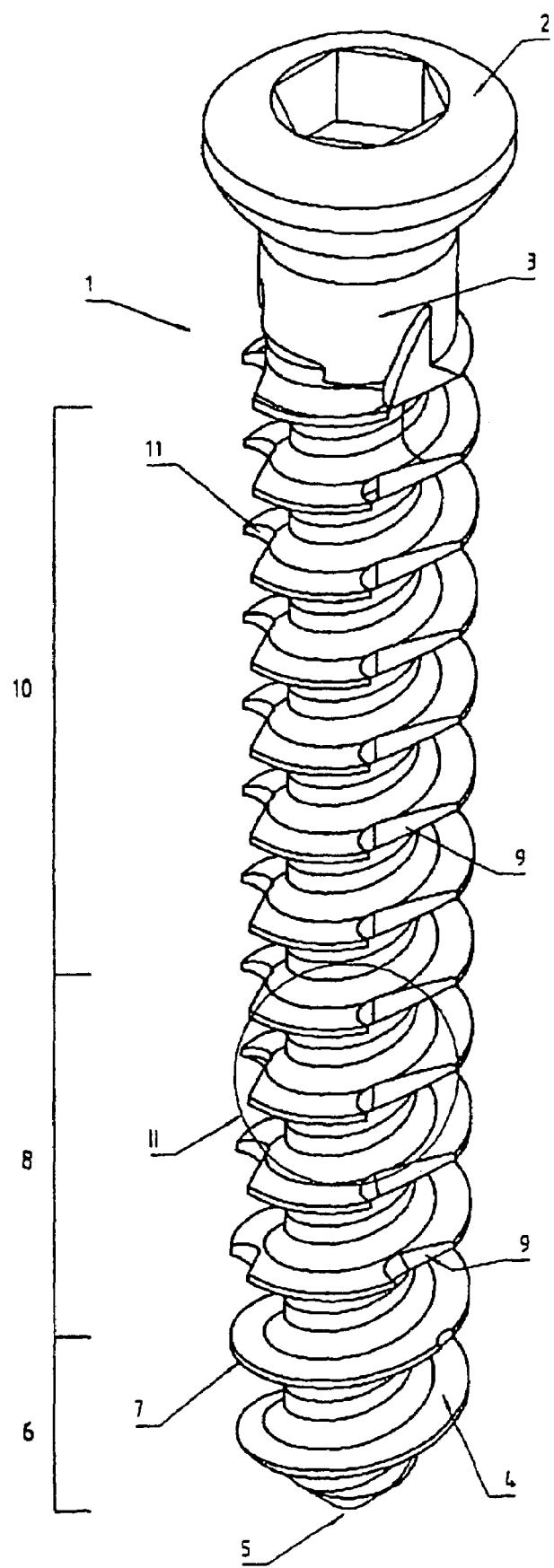
FIG. 1 is a perspective illustration of a bone screw.
Figure 2:
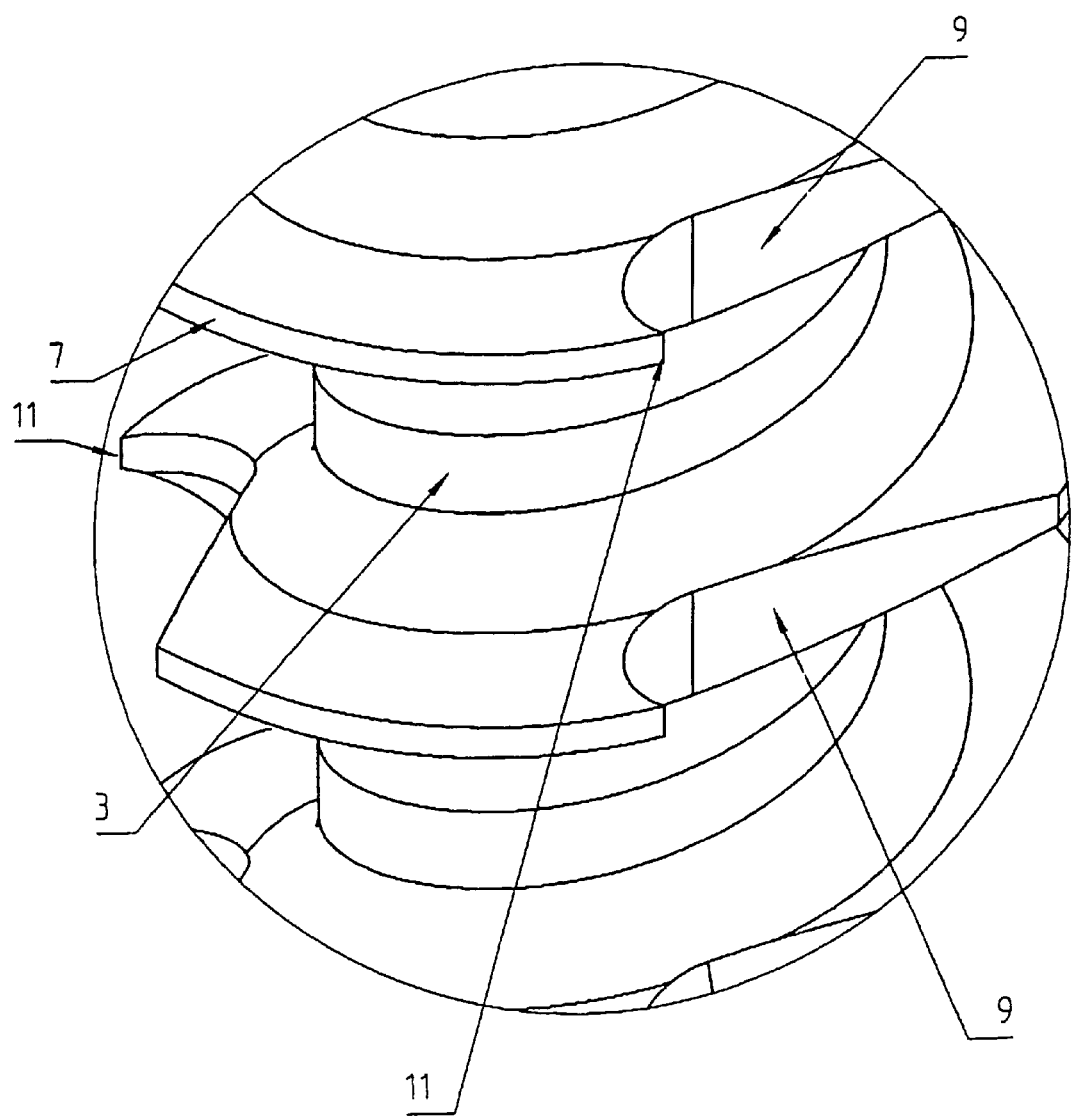
FIG. 2 is detail II from FIG. 1.
Figure 3:
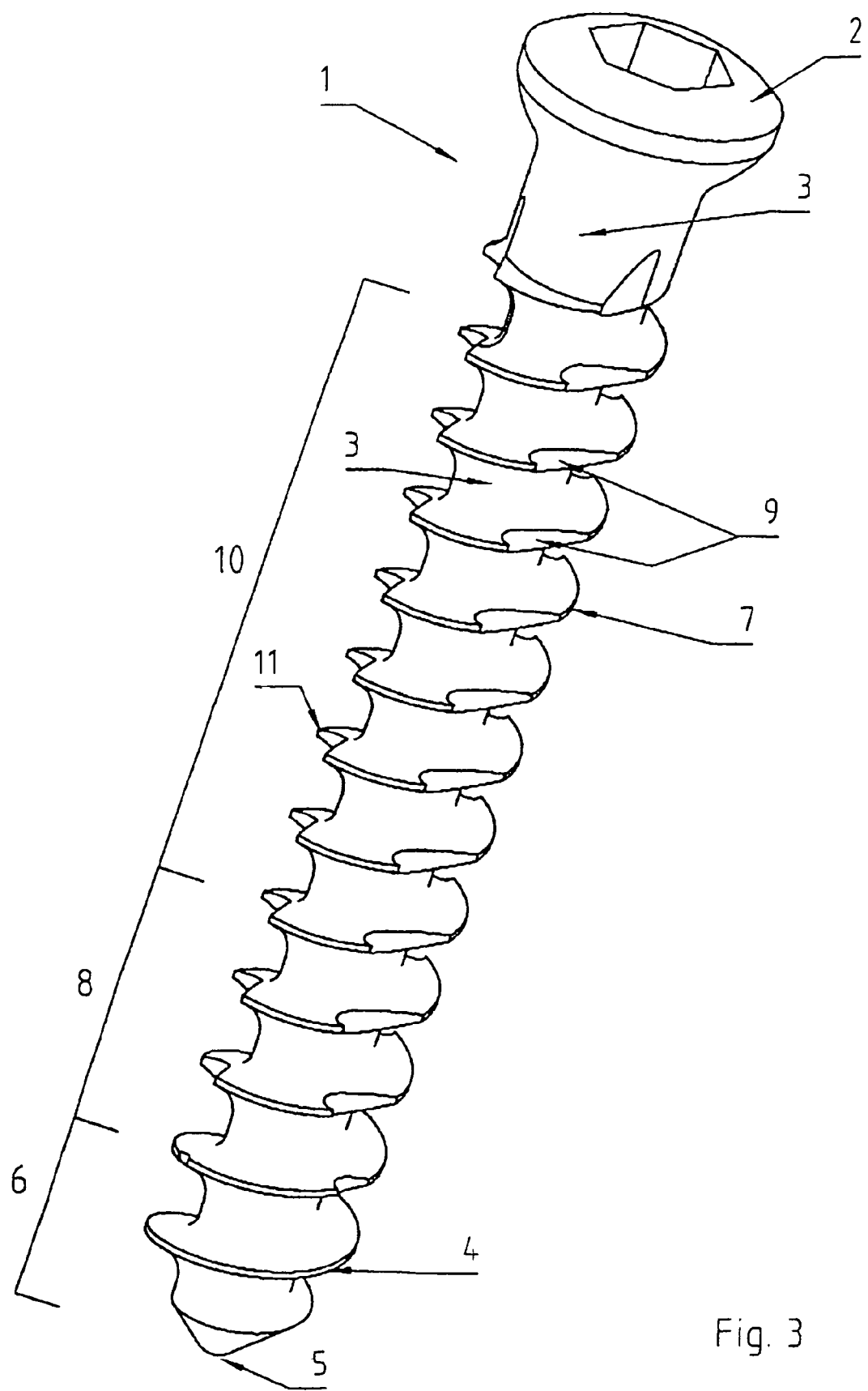
FIG. 3 is a perspective illustration of the bone screw from FIG. 1 from another view angle.
Figure 4:
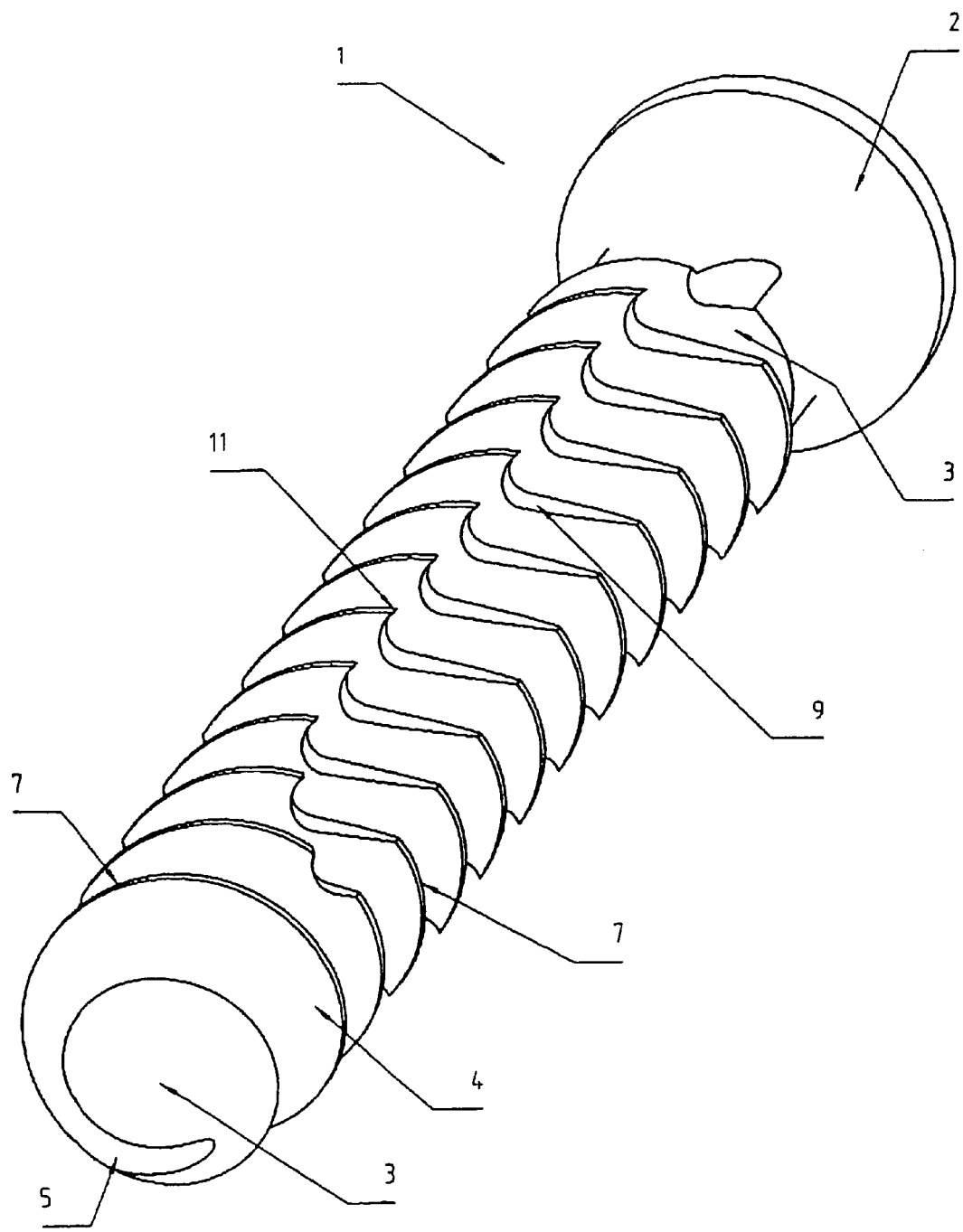
FIG. 4 is a perspective illustration of the bone screw from FIG. 1 from still another view angle.
Figure 5:
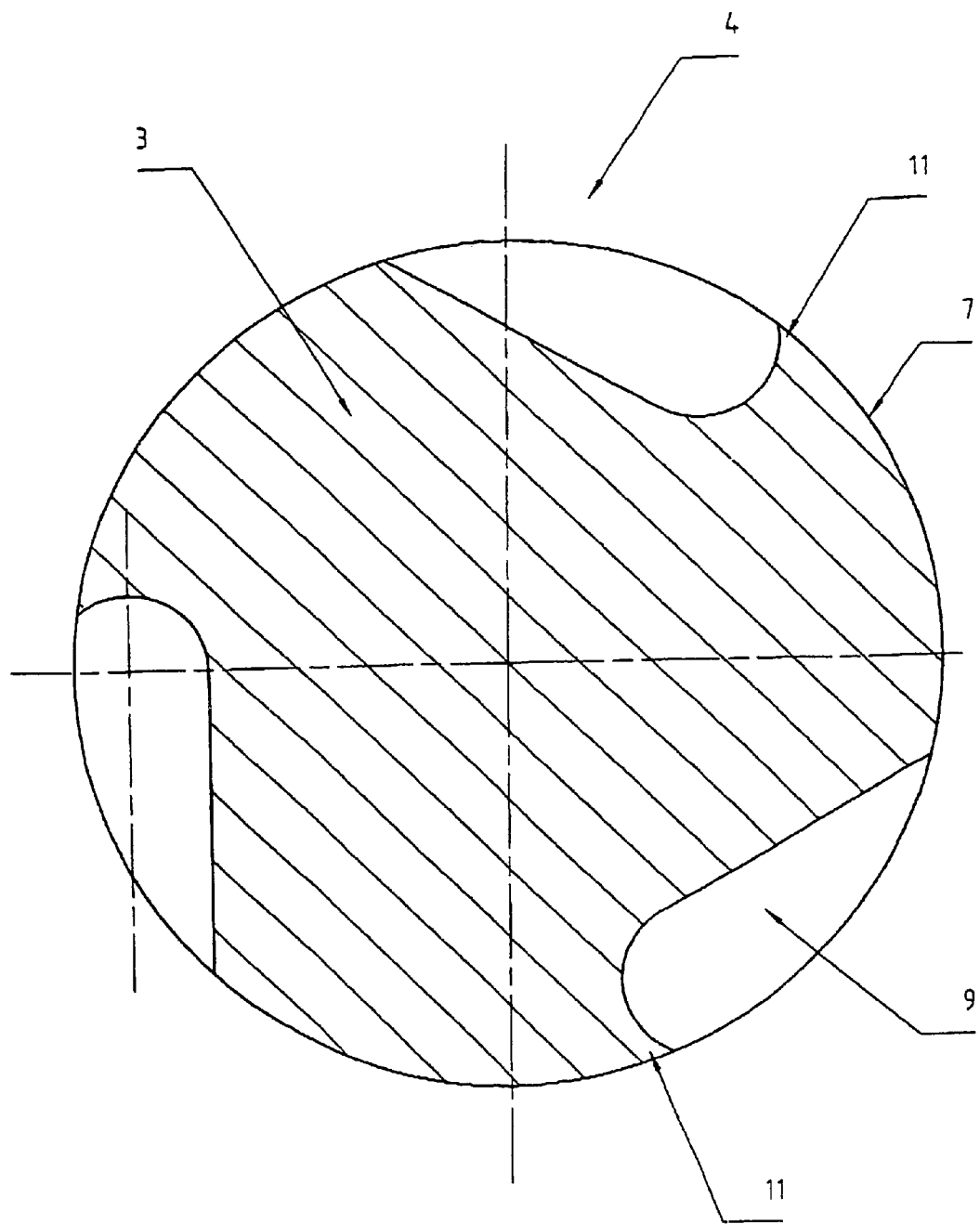
FIG. 5 is a cross section through the bone screw according to the invention.

The drawing shows a bone screw 1 that comprises a screw head 2, a screw shank 3 and a thread 4 formed from a plurality of turns on the screw shank 3. Starting from a free end 5 of the screw shank 3, several turns whose cutting edges 7 are smooth are combined to form a first screwthread 6. A second screwthread 8 is formed adjacent the first screwthread 6 toward the screw head 2 with recesses 9 formed in its cutting edges 7, three such recesses 9 equispaced every 360°. Especially from FIG. 3 it can be seen that the recesses 9 of the second screwthread 8 relative to the angular length in circumferential direction are increased compared to the second screwthread 8 preceding respectively from the free end 5 of the screw shank 3, i.e. that in the second screwthread 8 the angular length of the cutting edges 7 shortens toward the screw head 2 in favor of an increase of the length of the recesses 9. It can be also seen in FIG. 3, that a third screwthread 10 extends from the second screwthread 8 and has recesses 9 that are all identical. The detailed illustration in FIG. 2 as well as the section from FIG. 5 show that the recesses 9 extend chordally toward the screw shank 3 from the cutting edges 7 of the second screwthread 8 and of the third screwthread 10 and join in an arc with the cutting edge 7, such that barbs 11 are formed that offer resistance to unscrewing of the bone screw 1.

The embodiment represented in the drawing has a screw shank 3 that has a cylindrical form, wherein also the possibility exists that the screw shank 3 has a tapered form, with which it is suggested that the length of the cutting edges 7 of the second screwthread 8 is constant.

The invention claimed is:

1. A bone screw comprising:
   an elongated cylindrical shank having a free end and at an opposite end a screw head;
   a screwthread extending generally helically along the shank from the free end toward the screw head and itself having
      a first screwthread portion extending from the free end toward the screw head, comprising three turns, and forming a generally continuous and smooth cutting edge,
      a second screwthread portion extending from the first portion toward the screw head and formed of a plurality of turns each formed with at least one respective outwardly open recess, the recesses being of increasing angular dimension away from the free end, and
      a third screwthread portion extending from the second portion to the screw head and formed of a plurality of turns each formed with three outwardly open recesses equispaced every 360°, all of the recesses of the third portion being of generally the same angular dimension.

2. The bone screw according to claim 1 wherein in the second screwthread portion and in the third screwthread portion every 360° several recesses are formed.

3. The bone screw according to claim 2 wherein every 360° three recesses are formed.

4. The bone screw according to claim 1 wherein each recess extends as a chord toward the screw shank from the cutting edges of the second screwthread portion and of the third screwthread portion and joins in an arc again the respective cutting edge.

5. The bone screw according to claim 1 wherein the second screwthread portion comprises three turns.

6. The bone screw according to claim 1 wherein lengths of the cutting edges of the turns of the second screwthread portion are constant.

7. The bone screw defined in claim 1 wherein the angular dimension of the recesses of the third portion corresponds substantially to the angular dimension of that turn of the second portion closest to the third portion.

8. The bone screw defined in claim 1 wherein the recesses of the third screwthread portion have a radial depth that is less than a radial height of the turns of the screwthread portion.

9. The bone screw defined in claim 1 wherein the turns of the second and third screwthread portions are each formed with at least three of the respective recesses.

* * * * *